US00PP29924P3

(12) United States Plant Patent
Hansen

(10) Patent No.: US PP29,924 P3
(45) Date of Patent: Nov. 27, 2018

(54) ***HEUCHERA* PLANT NAMED 'ELECTRIC PLUM'**

(50) Latin Name: ***Heuchera* hybrid**
Varietal Denomination: Electric Plum

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 33 days.

(21) Appl. No.: 15/530,319

(22) Filed: Dec. 21, 2016

(65) Prior Publication Data

US 2018/0177102 P1 Jun. 21, 2018

(51) Int. Cl.
*A01H 5/02* (2018.01)
*A01H 5/12* (2018.01)

(52) U.S. Cl.
USPC ..... Plt./440
CPC ..... *A01H 5/02* (2013.01); *A01H 5/12* (2013.01)

(58) Field of Classification Search
USPC ..... Plt./440
See application file for complete search history.

*Primary Examiner* — Keith O. Robinson

(57) ABSTRACT

A new and distinct hybrid of *Heuchera* plant named 'Electric Plum' with cordate, dark, blackish-purple, shallowly dissected foliage in early spring developing into plum-purple blush with contrasting blackish purple surrounding the veins. The new plant is adorned with blackish purple panicles beginning in early summer with bright fuchsia-pink flowers beginning early summer for about seven weeks with repeat panicles.

1 Drawing Sheet

Botanical denomination: *Heuchera* hybrid.
Variety denomination: 'Electric Plum'.

BACKGROUND OF THE INVENTION

The present invention relates to a new and distinct cultivar of Coral Bells in the Saxifragaceae family and given the cultivar name of 'Electric Plum'. *Heuchera* 'Electric Plum' was hybridized by the inventor on Apr. 13, 2013 at a wholesale perennial nursery in Zeeland, Mich., USA. The seed or female parent was a proprietary unreleased hybrid known only by the breeder code 12-29-01 (not patented) and the pollen or male parent was *Heuchera* 'Georgia Plum' U.S. Plant Pat. No. 24,507. The female parent consists of genes from 'Mocha Mint' (not patented) 'Blackberry Ice' U.S. Plant Pat. No. 26,788 and 'Milan' U.S. Plant Pat. No. 21,682.

The new invention has a mixture of *Heuchera americana, H. brizoides, H. micrantha, sanguinea* and *H. villosa* in the pedigree.

*Heuchera* 'Electric Plum' was initially evaluated in the fall of 2013 and passed final evaluation in the fall of 2014 when it was assigned the breeder code 13-715-1 from among thousands of other seedlings from the same cross and hundreds of other crosses. *Heuchera* 'Electric Plum' has been asexually propagated by division at the same nursery in Zeeland, Mich. in 2014 and by careful sterile shoot tip tissue culture propagation, and the resultant plants have remained stable and continued to exhibit the same characteristics as the original plant for multiple generations.

No plants of *Heuchera* 'Electric Plum' have been sold or disclosed by this or any other name, in this country or anywhere in the world, prior to one year from the filing of this application, with the exception of that which was either derived directly or indirectly from the inventor.

BRIEF SUMMARY OP THE INVENTION

In comparison to the ancestor cultivars on the female side, *Heuchera* 'Electric Plum' has more shallowly lobed leaves with purple base rather than the reddish base with heavy silver overlay between the veins of 'Milan'. The new plant has similarly shallow lobed foliage as 'Mocha Mint' but has more plum coloration without the silver overlay. Compared to 'Blackberry Ice' the new plant has more purple in the foliage and the flowers are fuchsia pink rather than creamy white. Compared with 'Plum Royale' U.S. Plant Pat. No. 20,935 the new plant has bright fuchsia pink flowers rather than creamy-colored flowers, wider dark blackish purple surrounding the veins and lighter plum between the veins. Compared to 'Georgia Plum' the new plant has more rounded lobe apices and without the silvering between the veins.

*Heuchera* 'Electric Plum' differs from its parents as well as all other coral bells known to the applicant in the following combined traits:

1. The foliage color is dark blackish-purple early in the spring.
2. Foliage develops a plum-purple blush with contrasting dark blackish purple surrounding the veins.
3. Adorned with small, bright, fuchsia-pink flowers on blackish purple panicles beginning in early summer.
4. Leaves are cordate with shallowly dissected rounded apices and lobes.

BRIEF DESCRIPTION OF THE DRAWINGS

The photographs of the new plant demonstrate the overall appearance of the plant including the unique traits. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
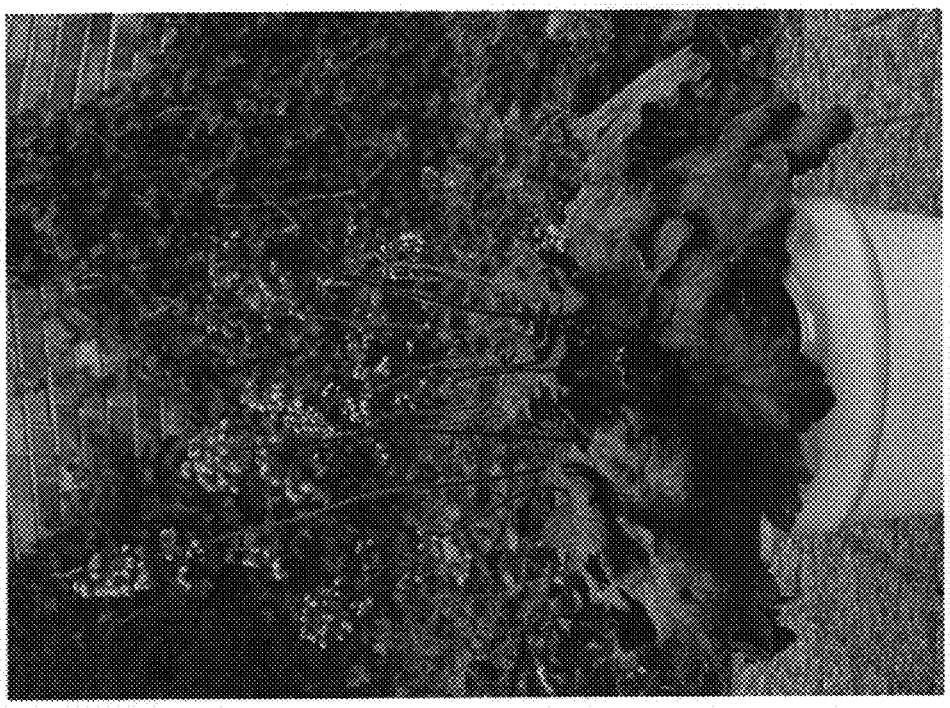
FIG. 1 shows a two-year-old plant in late spring with plum-purple blush.
Figure 2:
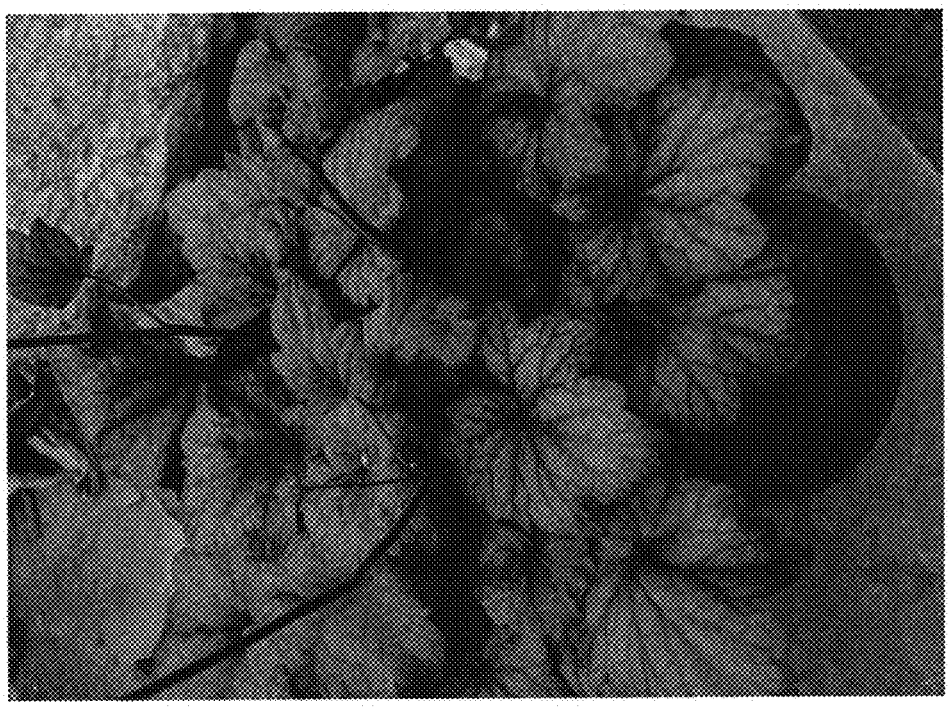
FIG. 2 shows a two-year-old plant in a container in mid-season flowering.

The following description is based on one and two-year-old plants growing in a container in a lightly shaded greenhouse in Zeeland, Mich., USA. The new plant has not been grown under all possible environments and may phenotypically appear different under different conditions such as light, temperatures, fertilizer, and water, without any difference in genotype. The color descriptions used are from the 2001 edition of The Royal Horticultural Society Colour Chart except where common dictionary terms are used.

Parentage: Female or seed parent was the proprietary unreleased hybrid known only by the breeder code 12-29-01 (not patented), and the pollen or male parent was 'Georgia Plum';

Plant habit: Hardy herbaceous perennial with compact basal rosette of foliage; mounded foliage about 15.0 cm tall and 35.0 cm in diameter; with about 4 to 5 panicles per stem, to about 44.0 cm long; stems to about 4.0 mm diameter at base, with one main stem and about 3 developing stems per plant and about 100 leaves per plant;

Roots: Fibrous, finely branched;

Growth rate: Rapid, rooting from cutting in two weeks and finishing in three-liter container in about 10 weeks;

Foliage: Cordate, minutely puberulent adaxial and abaxial; palmately shallowly lobed with five main lobes dissected less than one-quarter the way to petiole; apex rounded to apiculate, base cordate to auriculate with basal lobes slightly imbricate; margins crenate to mucronate, ciliolate; lustrous abaxial and matte adaxial; held nearly horizontal;

Leaf blade size: To about 12.0 cm wide and about 12.5 cm long, average about 10.0 cm wide and about 10.5 cm long;

Leaf color: Spring and young emerging leaves adaxial nearest RHS 187B, spring and young emerging leaves abaxial between RHS 187C and RHS 187B; mature mid-season leaves adaxial blend between RHS 71A and RHS 187A with region surrounding veins of nearest RHS N186A, abaxial mature mid-season leaves between RHS N186b and RHS N186C;

Leaf quantity: Dense, about 80 per plant;

Veins: Palmate, hirsutulous abaxial and adaxial; costate abaxial, mostly applanate adaxial;

Vein color: On emerging or early spring foliage adaxial nearest RHS 185B with emerging or early spring abaxial nearest RHS 71A; mid-season and flowering time adaxial nearest RHS N186A, mid-season and flowering time abaxial RHS N79B;

Petiole: Terete, with amplexicaul base; to about 14.0 cm long and about 4.0 mm diameter above stipule; stipule to about 10.0 mm across and 5.0 mm long; average about 12.0 cm long and 3.2 mm diameter with pubescent hairs to about 2.0 mm long;

Petiole color: Emerging leaf blend nearest RHS 71A; mature leaf near base of petiole nearest RHS 186A with stipples or flecks of nearest RHS 187B;

Peduncle: Panicle; terete; stiff; puberulent; mostly upright; to about 44.0 cm long and about 4.0 mm diameter at base, average about 38.0 cm tall and about 3.5 mm diameter; about thirteen per plant with up to 135 flowers per panicle, average about 100; branched panicle with up to up to 14 branches up to 4.5 cm long and 1.0 diameter decreasing distally, average 12 branches per panicle; shorter branches outwardly, longer branches drooping distally, Flowering longevity: Panicle effective for about three weeks; repeating for about seven weeks;

Peduncle color: Young developing nearest RHS 187B, mature blend between RHS 187A and RHS N186B;

Pedicel: Terete, finely pubescent, average about 3.0 mm long and 0.5 mm diameter;

Pedicel color: Between RHS N186A and RHS 187A;

Buds one day prior to opening: Ellipsoid; rounded apex and attenuate base; puberulent to glandular; about 7.0 mm long and 3.5 mm diameter;

Bud color one day prior to opening: Basal one-half portion nearest RHS 60C, distal one-half between RHS 63B and RHS 63C with apex nearest RHS 61A;

Flower: Perfect, campanulate, actinomorphic, about 9.0 mm long from base to end of stigma and 4.5 mm in diameter at face; individual flowers lasting about 4 days on plant; three weeks for whole inflorescence and seven weeks with repeat panicles;

Flower color: Overall effect bright fuchsia pink;

Flower density: Sparse;

Flower attitude: Outward to slightly drooping;

Calyx: Five, apex rounded; fused in proximal 4.0 mm to form hypanthium; pubescent to glandular abaxial, glabrous adaxial; about 7.0 mm long and 4.5 mm wide;

Calyx color: Abaxial base between RHS 59A and RHS 61A with longitudinal center nearest RHS 71B and distally lightening to between RHS 64B and RHS 64C; adaxial base nearest RHS 64C with longitudinal middle portion nearest RHS 65D and apex nearest RHS 61A;

Petals: Five, oblanceolate to spatulate, acute apex and attenuate base, entire, glabrous abaxial and adaxial, about 3.5 mm long and 1.0 mm wide in middle;

Petal color: Abaxial and adaxial base lighter than RHS N155D; abaxial apex between RHS 64B and RHS 64C, abaxial apex between RHS 64D and RHS 64C;

Androecium: Five adnate to adaxial sepal about 1.0 mm above base;

*Filaments*.—Five, thin, glabrous; about 2.5 mm long and less than 0.3 mm diameter; color white, lighter than RHS N155D.

*Anthers*.—Ellipsoidal with acute apex; distinct, basifixed, longitudinal; about 0.7 mm long and 0.5 mm across; color nearest RHS 167C.

*Pollen*.—Rare to absent.

Gynoecium: One, two-beaked; half-inferior; bifid style with pistil split at ovary; 7.0 mm long;

*Style*.—Bifid; split apart at apex of ovary; about 5.0 mm long and about 1.0 mm diameter; color nearest RHS 155D.

*Stigma*.—Rounded apex, about 0.5 mm diameter; color nearest RHS 60D.

*Ovary*.—Half-inferior, about 2.0 mm long and 1.5 mm diameter; ellipsoidal to globose, base rounded; color nearest RHS 145D.

Fruit and seed have not yet been observed;

Disease and pest tolerance: The new plant grows best with ample moisture and drainage in either part sun or part shade. Cold hardy from USDA zones 4 to 9. Other resistance and tolerance outside of that normal for coral bells has not been observed. Under trial and production growing conditions in Michigan 'Electric Plum' has not been found to be affected by *Puccinia heucherae, Pseudomonas syringae, Xanthomonas campestris, Colletotrichum* sp. or *Botrytis cinerea.*

It is claimed:

1. A new and distinct coral bells plant named 'Electric Plum' as herein described and illustrated.

* * * * *